United States Patent [19]

Ledergerber

[11] Patent Number: 5,723,006
[45] Date of Patent: Mar. 3, 1998

[54] BREAST IMPLANT INTRODUCER

[76] Inventor: Walter J. Ledergerber, 31 Morningwood, Laguna Niguel, Calif. 92677

[21] Appl. No.: 646,845

[22] Filed: May 8, 1996

Related U.S. Application Data

[63] Continuation of Ser. No. 272,907, Jul. 8, 1994, Pat. No. 5,571,178, which is a continuation of Ser. No. 73,966, Jun. 8, 1993, abandoned, which is a continuation of Ser. No. 660,290, Feb. 22, 1991, abandoned.

[51] Int. Cl.⁶ .............................. A61F 2/12; A61B 17/02
[52] U.S. Cl. ........................ 623/8; 600/233; 623/66
[58] Field of Search ................ 623/8, 66; 600/204, 600/233, 208, 210

[56] References Cited

U.S. PATENT DOCUMENTS

| | | | |
|---|---|---|---|
| 747,444 | 12/1903 | La Veine | 604/59 |
| 977,004 | 11/1910 | Grimm | 604/59 |
| 2,053,868 | 9/1936 | Grosso | 128/20 |
| 2,509,241 | 5/1950 | Mende | 604/11 |
| 2,587,364 | 2/1952 | Mitchell | 604/59 |
| 2,754,823 | 7/1956 | Miller | 604/59 |
| 2,812,758 | 11/1957 | Blumenschein | 600/208 |
| 3,129,706 | 4/1964 | Reynolds, Jr. | 128/20 |
| 3,714,943 | 2/1973 | Yanof et al. | 604/70 |
| 3,807,393 | 4/1974 | McDonald | 600/208 |
| 3,853,125 | 12/1974 | Clark et al. | 604/70 |
| 4,035,850 | 7/1977 | Cresswall | 623/8 |
| 4,143,428 | 3/1979 | Cohen | 623/8 |
| 4,413,986 | 11/1983 | Jacobs | 604/14 |
| 4,421,508 | 12/1983 | Cohen | 604/70 |
| 4,610,659 | 9/1986 | Friese | 604/15 |
| 4,624,671 | 11/1986 | Kress | 623/8 |
| 4,798,584 | 1/1989 | Hancock et al. | 623/8 |
| 4,834,094 | 5/1989 | Patton et al. | 606/107 |
| 4,955,906 | 9/1990 | Coggins et al. | 623/8 |
| 5,123,905 | 6/1992 | Kelman | 606/107 |
| 5,159,921 | 11/1992 | Hoover | 600/208 |
| 5,345,927 | 9/1994 | Bonutti | 600/208 |
| 5,454,365 | 10/1995 | Bonutti | 600/204 |
| 5,520,610 | 5/1996 | Giglio et al. | 600/208 |
| 5,522,790 | 6/1996 | Moll et al. | 600/208 |

*Primary Examiner*—David Isabella
*Attorney, Agent, or Firm*—Lyon & Lyon LLP

[57] ABSTRACT

A tool and method for introducing an implant through an incision in a body utilizing a tube having a hole through which the implant is pressed. In the preferred embodiment, a two part tube has one opened end and one closed end. The tube contains an expanding structure, for applying pressure on the implant, optionally a pressure transmitting structure, and an implant. The expanding structure is expanded optionally by gas or fluid filling the structure. Optionally, a collar is disposed around the tube near the opening, selectively covering and uncovering a cut-out in the tube which permits manipulation of the implant prior to insertion.

2 Claims, 3 Drawing Sheets

BREAST IMPLANT INTRODUCER

This is a continuation of application Ser. No. 08/272,907, filed Jul. 8, 1994, U.S. Pat. No. 5,571,178, which is a continuation of application Ser. No. 08/073,966, filed Jun. 8, 1993, now abandoned, which is a continuation of Ser. No. 07/660,290, filed Feb. 22, 1991, now abandoned.

BACKGROUND OF THE INVENTION

Reconstruction of the human breast involves introducing a fixed or changeable-volume sac-like silicone rubber structure into a body cavity surgically created to receive such an implant. The implants and coverings therefor are described, by way of illustration and not by limitation, in: Braumann U.S. Pat. No. 4,648,880; Hamas U.S. Pat. No. 4,531,244; and Ledergerber U.S. Pat. No. 4,955,907.

The usual skin incision is on the order of 3–8 centimeters in length and is stretched open with retractors to facilitate the introduction of the implant. By virtue of the displacement of fluid contained in the sac-like implant from outside of the body into the portion of the sac which has been introduced into the implant cavity, it is possible to gradually advance the membrane of the sac in pursuit of its fluid contents.

A number of sheet-like structures have been utilized to facilitate the introduction of implants into the body by enveloping the implant, with the primary object being to shape the fluid-filled sac for presentation to the retracted wound margins. The use of these sheet-like devices has not been of benefit in the hands of many practitioners of the art.

With advancing technology in breast implant design have come new designs exhibiting textured as opposed to smooth surfaces which are brought into intimate contact with the patient's tissues in the implanted state. A variety of textured surfaces for implants are disclosed in my issued U.S. Pat. No. 4,955,907, incorporated herein by reference. Since breast implants are usually placed into the body through incisions considerably smaller than the implant, it has always been a challenge to introduce them. With greatly increased friction at the interface between the surface of newer texturized implants and the wound margins (body tissue), it has become correspondingly more difficult to introduce these implants. Increased manipulation of both implants and patient tissue often results in trauma to both implants and patient tissue, thereby increasing the risk associated with the procedure both in terms of immediate consequences as well as delayed structural failure and the implications deriving therefrom. It has become a matter of some urgency to be able to introduce breast implants atraumatically.

SUMMARY OF THE INVENTION

A new breast implant introducer has as its object the alleviation of the difficulty of introducing breast implants and thus limiting greatly both damage to implants and trauma to patient tissues. In one of the preferred embodiments, a two-part rigid or flexible tube has one open end and one closed end. The two parts of the tube are held in apposition by closure means in order to create a single large cavity: the large cavity contains three soft structures (in the present preferred embodiment) including the breast implant which is extruded out of the open end of the tube upon increasing the pressure inside the topmost soft structure.

The topmost soft structure is expanded by introducing fluid or a gas by actuating the pump which may be connected to a fluid reservoir if fluid is utilized, or may simply be combined with a valve for gas intake and/or exhaust. The expanding medium in the topmost soft structure applies pressure to the middle soft structure which in turn applies pressure to the lowest structure, the implant. The implant is extruded via the open end of the flexible or rigid structure. A soft or rigid collar assists in containing the implant within the neck of the tube during extrusion.

In another embodiment, a flexible tube has two open ends, one large enough to receive the implant, and the other small enough to insert the implant into the wound. In this embodiment, the tube is flexible, and permits direct user application of force through the flexible tube onto the implant. Optionally, a relatively rigid ring or partial annulus is affixed to the smaller opening. The ring or partial annulus may be placed partially inside the wound to stabilize the implant introducer tube.

A generally circular retractor adapted for use with the implant introducer is sized to be placed inside the wound when unexpanded, and to expand out, thereby facilitating implant introduction.

Accordingly, it is a principal object of this invention to provide a useful structure and method for introducing an implant through an incision in the human body.

It is a further object of the invention to provide for atraumatic introduction of an implant.

BRIEF DESCRIPTION OF THE DRAWINGS

The above objects and advantages of this invention will be more easily understood with reference to the following drawings and detailed descriptions.

DETAILED DESCRIPTION OF THE PREFERRED EMBODIMENTS AND THEIR OPERATION IN USE

Figure 1:
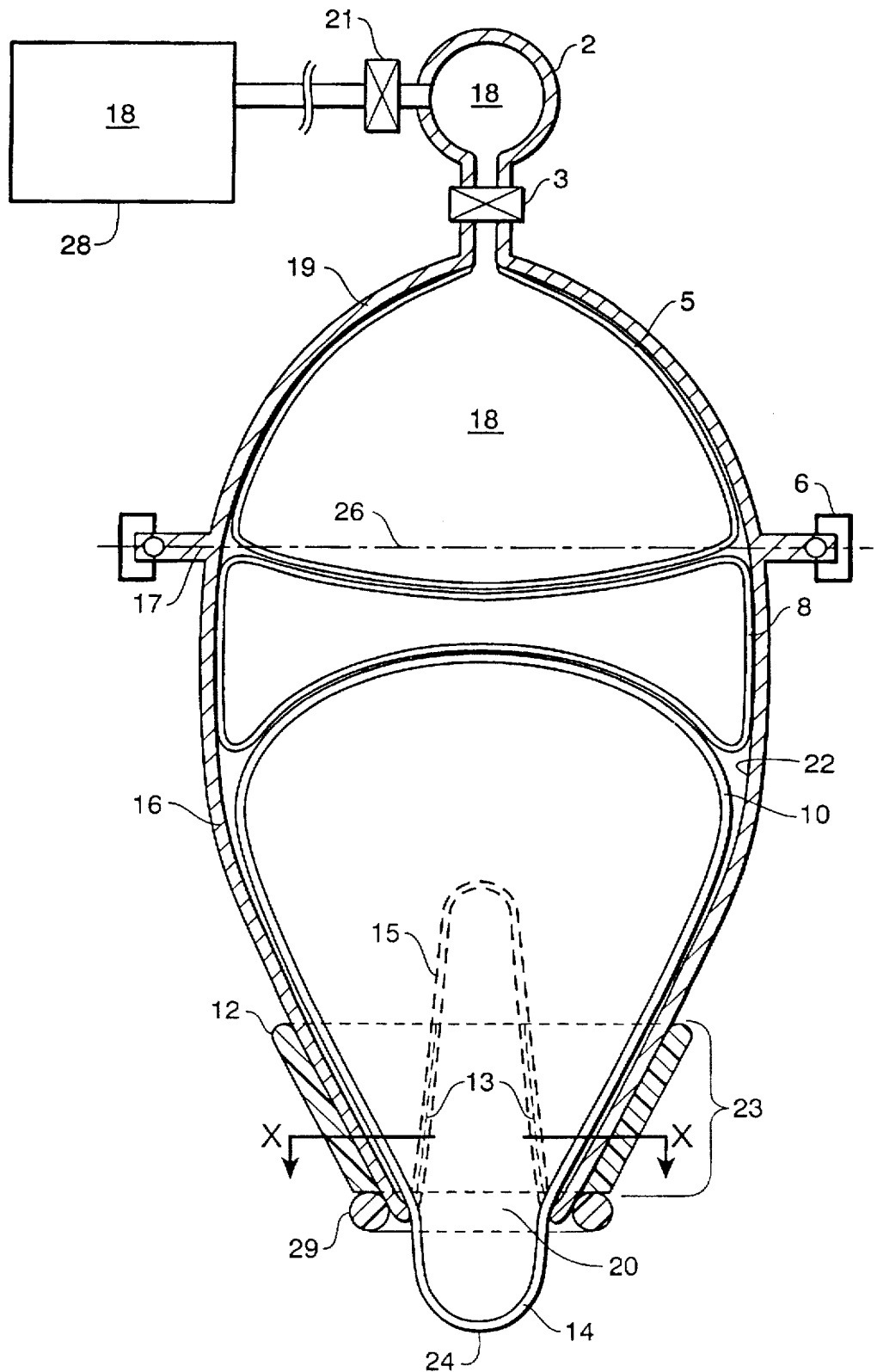
FIG. 1 is a cross-section of a breast implant introducer.

Referring to FIG. 1, a rigid tube 16 and a rigid cup 19 in which these structures may be hinged to each other to permit closure and thereby create a single joined structure, may have as its inner wall 22 a highly polished or otherwise treated surface with a very low coefficient of friction. A pump 2 with valves 3, 21 and possibly a fluid reservoir, are provided.

Two or three soft structures 5, 8, and 10 are enclosed within the combined tube and cup structure, one of which is an expansible structure 5 and another of which is the breast implant 10. A third structure 8 may be optionally interposed between the expansible structure 5 and the implant 10 for the purpose of limiting trauma to the implant 10 and also to provide for uniform transmission of pressure from the expansible structure to the implant.

Figure 2:
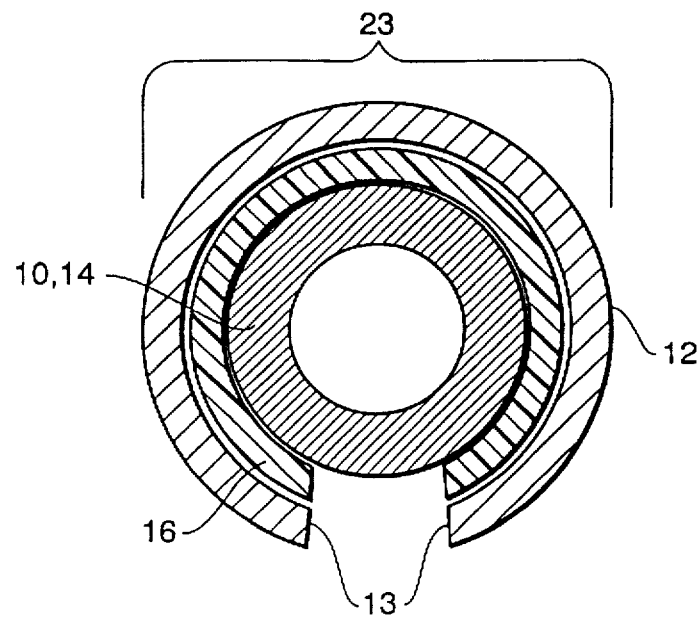
FIG. 2 is a sectional view of FIG. 1 at "X—X".

Referring to FIG. 2, the collar 12 is positioned relative to the rigid or flexible tube 16 in such a way that a relief gap/void or cut-out in each superimposes on the other in such a way that the implant can be grasped or otherwise manipulated by the surgeon's fingers during the early "loading phase" during operation of the device. During active extrusion of the implant the collar 12 is rotated 180 degrees from its loading position in order to present a barrier to the transversely expanding portion of the implant.

Optionally, a relatively rigid ring or partial annulus 29 may be disposed at the end of the implant introducer which is used adjacent the body. The ring may be disposed inside the wound, and serve to stabilize the introducer during insertion of the implant.

In operation, with the rigid cup/tube combined structure open, the implant is introduced in the tube 16 portion and pushed toward the smaller open end 20 of the tube 16. The surgeon grasps the leading edge 24 of the implant through the relief gap/void/cut-out 13 while advancing the leading edge 24 of the implant through the neck 23 and part way through the open end 20 of the tube 16. A second soft structure 8 is placed on top of the implant 10 and thus positioned between the implant 10 and the expansible soft structure 5 in the rigid cup 19 portion of the combined cup/tube structure. The combined cup/tube structure is then closed and sealed by utilizing optional closure/locking means 6. Pump 2 is actuated to expand the expansible soft structure 5 sufficient to exert pressure through the middle soft structure 8 onto the implant 10. The collar 12 is turned 180 degrees in such a way that the body of the collar 25 presents a barrier to transverse expansion of that portion of the implant 10 positioned in the neck 23 of the tube 16. Further expansion of the expansible structure 5 by filling with fluid or gas 18 forces the implant to be extruded via the opening 20 in the tube 16. The leading lobe 14 of the implant is positioned directly over the incision through which it is to be introduced into the implant cavity of the patient. Additional actuation of the pump 2 completes extrusion of the implant 10. During final extrusion the surgeon's hands stabilize the neck 23 and collar 12 as well as the cup 19 or pump 2 portions of the invented device.

Another embodiment of the device is that where the cup 19 and tube 16 are rigid and the expansible structure 5 is a rigid sliding piston-like element and where the middle structure 8 may be either a sac-like structure or a sliding piston-like structure.

Another embodiment of the device is that where the cup 19 and tube 16 are flexible and sheet-like and either joined as are the cup 19 and tube 16 above or joined by virtue of being made of the same piece of flexible material. In this embodiment the implant 10 is loaded into the device through the large opening at the end opposite the open extrusion end 20 exactly as described above. Extrusion of the implant 10 results upon closing the end through which the implant was loaded by twisting, folding, rolling, constricting, or otherwise closing and by applying and maintaining hand and digital pressure external to the flexible cup/tube combined structure while stabilizing the neck 23 as well as the closed end of the device with the surgeon's hands. The ring may be positioned inside the body cavity created to receive the implant. Preferred sheet-like material of the ring—is a semi-dense biocompatible rubber compound. Preferred materials for this embodiment include Gore-Tex (PTFEe, expanded polytetrafluoroethylene) as well as other materials exhibiting low coefficients of friction.

Preferred materials for the rigid embodiments of cup 19 and tube 16 as described above include teflon, nylon, polyethylene and other plastic polymers as well as metals including stainless steel, annealed glass, and others.

The preferred fluid 18 for filling of the expansible chamber 5 is normal saline solution. Other fluids may also be suitable.

One of the preferred gases 18 for filling the expansible chamber 5 is room air.

The preferred embodiment of the pump 2 described above may be a hand actuated pump. The position of the pump 2 with respect to the rigid or flexible structures 19 and 16 described above is variable and dependent only upon an efficient design of the entire invented device.

An expansible chamber 5 in another embodiment may be comprised of a rigid cup 19 and an expansible membrane 26 positioned and fixed to a cross-sectional perimeter of the rigid cup as, for example, along the seam plane 17.

Another preferred embodiment is that in which pressure is applied to implant 10 and structure 8 by a rigid or flexible metal or plastic piston which is advanced mechanically through the cup/tube combination along the long axis of the tube 19.

In connection with any embodiment of this invention, it may be desirable to include the implant within a sheet of slippery material, such as Gore-Tex, for easing insertion of the implant. Once the implant and sheet are introduced into the body, the sheet may be removed.

Figure 3A:
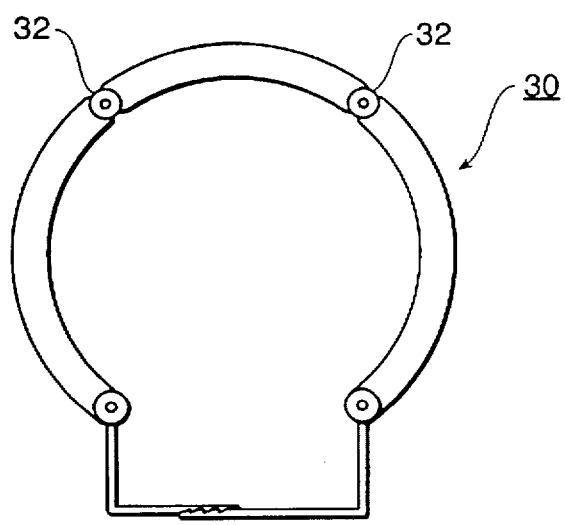
FIG. 3 shows a retractor for use with the introducer, in plan view and side view.
Figure 3B:
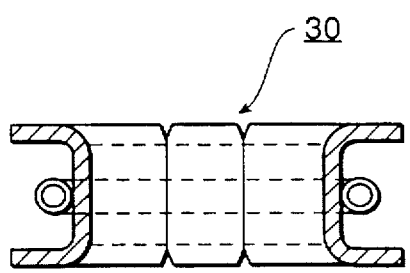
Figure 4:
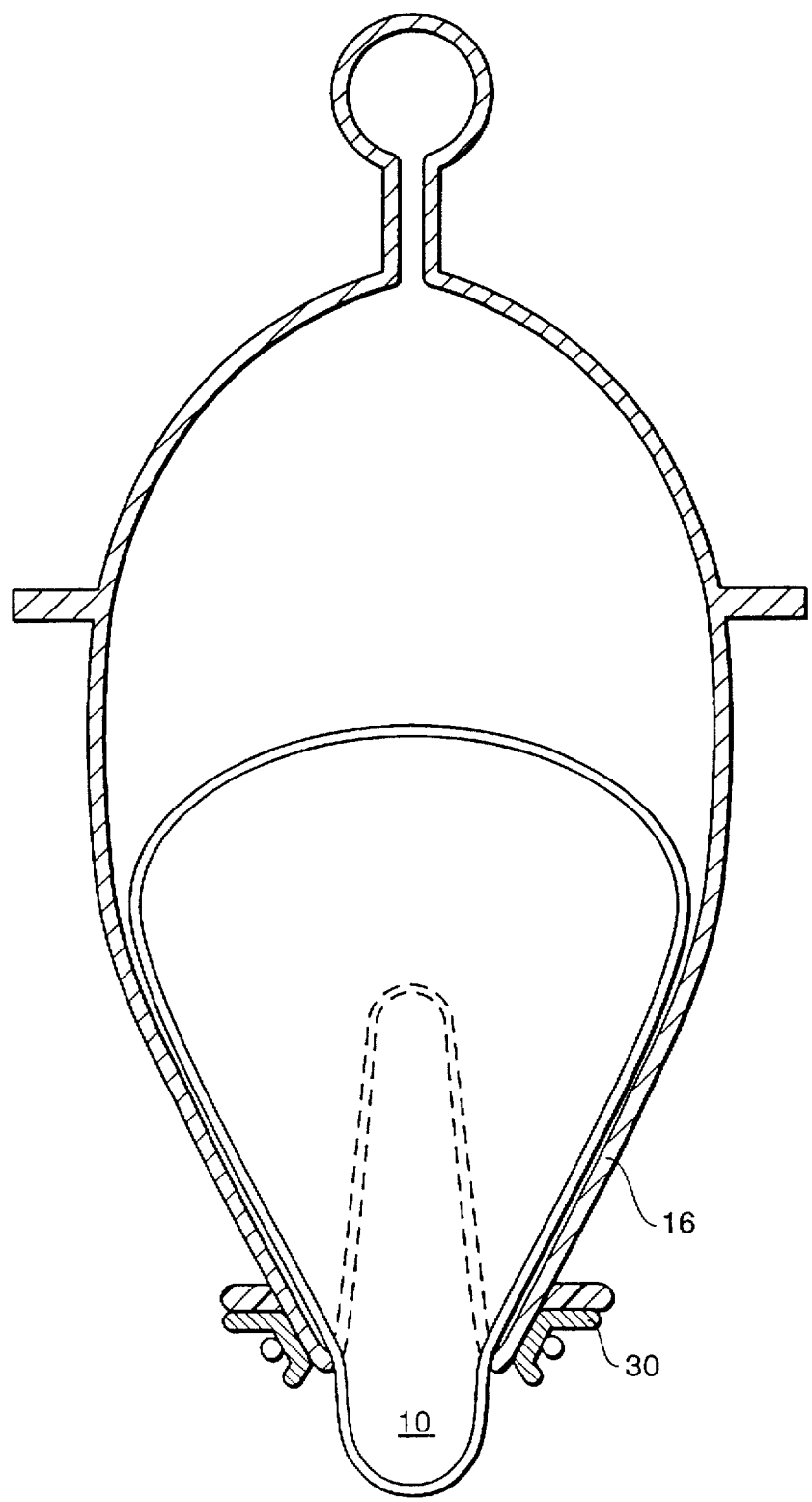
FIG. 4 shows an introducer in combination with the retractor.

FIG. 3 shows a self-retaining ring retractor for use in connection with the implant introducer of this invention. The retractor 30 is sized to be inserted into the wound when parially collapsed or folded, and then expanded to effect wound retraction for insertion of the implant. The retractor may be made of any suitable material, such as spring metal, or plastic or a dense rubber. It may be of one piece or may be segmented. Hinges 32 provide flexibility. As shown in FIG. 4, optionally, the implant inserter may be attachable to the ring retractor 30. In one embodiment, the implant introducer has a blade at the end for introduction of the implant, where the blade is retained by the ring retractor 30.

I claim:

1. A surgical implant introducer comprising a flexible tube having a first end and a second end, said first end having an opening sized to mate with an incision in a body, said second end having an opening sized to receive a surgical implant, said tube being closeable at said second end and deformable to force a surgical implant out of said opening of said first end of said tube, and a ring affixed to said first end of said tube adjacent said opening to stabilize said first end of said tube adjacent said opening during insertion of an implant into a body.

2. The surgical implant introducer of claim 1, further comprising a retractor to retract an incision in a body, said retractor being attachable to said ring adjacent said first end of said tube.

* * * * *

UNITED STATES PATENT AND TRADEMARK OFFICE
CERTIFICATE OF CORRECTION

PATENT NO. : 5,723,006
DATED : March 3, 1998
INVENTOR(S) : Ledergerber

It is certified that error appears in the above-identified patent and that said Letters Patent is hereby corrected as shown below:

At column 3, line 52, delete "sheet-like" and insert therefore --(sheet-like)--.

Signed and Sealed this

Twenty-ninth Day of June, 1999

Attest:

Q. TODD DICKINSON

*Attesting Officer*       *Acting Commissioner of Patents and Trademarks*